US006409755B1

(12) United States Patent
Vrba

(10) Patent No.: US 6,409,755 B1
(45) Date of Patent: *Jun. 25, 2002

(54) BALLOON EXPANDABLE STENT WITH A SELF-EXPANDING PORTION

(75) Inventor: Anthony C. Vrba, Maple Grove, MN (US)

(73) Assignee: Scimed Life Systems, Inc., Maple Grove, MN (US)

(*) Notice: Subject to any disclaimer, the term of this patent is extended or adjusted under 35 U.S.C. 154(b) by 1 day.

This patent is subject to a terminal disclaimer.

(21) Appl. No.: 09/710,520

(22) Filed: Nov. 9, 2000

Related U.S. Application Data

(63) Continuation of application No. 09/087,526, filed on May 29, 1997, now Pat. No. 6,168,621.

(51) Int. Cl.[7] .................................................. A61F 2/06
(52) U.S. Cl. ........................ 623/1.2; 623/1.12; 606/194
(58) Field of Search ............................ 623/1.15, 1.16, 623/1.18, 1.2, 1.27, 1.3, 1.31, 1.35, 1.11; 606/194

(56) References Cited

U.S. PATENT DOCUMENTS

| 5,226,913 A | * | 7/1993 | Pinchuk | 623/1 |
| 5,383,892 A | * | 1/1995 | Cardon et al. | 606/198 |
| 5,607,444 A | * | 3/1997 | Lam | 606/194 |
| 5,632,762 A |   | 5/1997 | Myler | |
| 5,639,278 A | * | 6/1997 | Dereume et al. | 623/1 |
| 5,643,312 A | * | 7/1997 | Fishell et al. | 606/198 |
| 5,723,003 A | * | 3/1998 | Winston et al. | 623/1 |
| 5,749,890 A |   | 5/1998 | Shaknovich | |
| 5,776,162 A |   | 7/1998 | Kleshinski | |
| 5,868,783 A | * | 2/1999 | Tower | 606/198 |
| 5,879,370 A | * | 3/1999 | Fischell et al. | 606/198 |
| 5,906,640 A | * | 5/1999 | Penn et al. | 623/1 |
| 6,017,363 A | * | 1/2000 | Hojeibane | 623/1.15 |
| 6,059,810 A |   | 6/2000 | Brown et al. | 606/198 |
| 6,168,621 B1 | * | 1/2001 | Vrba | 623/1.2 |
| 6,254,593 B1 | * | 3/2001 | Wilson | 606/1.11 |
| 6,273,910 B1 | * | 8/2001 | Limon | 623/1.15 |

FOREIGN PATENT DOCUMENTS

WO    WO 98/19628    5/1998

OTHER PUBLICATIONS

U.S. application No. 09/087,526, Vrba et al., filed May 29, 1998.

* cited by examiner

Primary Examiner—David H. Willse
Assistant Examiner—Suzette J. Jackson
(74) Attorney, Agent, or Firm—Vidas, Arrett & Steinkraus

(57) ABSTRACT

A stent consisting of at least two parts in juxtaposition, one part being of self-expandable characteristics while the other part is balloon expandable.

21 Claims, 4 Drawing Sheets

BALLOON EXPANDABLE STENT WITH A SELF-EXPANDING PORTION

CROSS REFERENCE TO RELATED APPLICATIONS

The instant application is a continuation of copending U.S. application Ser. No. 09/087,526 now U.S. Pat. No. 6,163,621, filed May 29, 1998 and incorporated herein by reference in its entirety.

FIELD OF THE INVENTION

The present invention relates to a new type of stent for transluminal implantation and in particular new vascular stents.

BACKGROUND OF THE INVENTION

Stents for transluminal implantation are well known. They are generally comprised of metallic supports which are inserted into a part of the human body such as bile ducts, the urinary system, the digestive tube and notably by percutaneous route inside the blood vessels, usually the arteries in which case they are typically termed vascular stents. Stents are usually generally cylindrical and are constructed and arranged to expand radially once in position within the body. They are usually inserted while they have a first relatively small diameter and implanted in a desired area, for example inside a vessel, then the stent is expanded in situ until it reaches a second diameter larger than the first diameter. A balloon associated with the catheter is usually used to provide the necessary interior radial force to the stent to cause it to expand radially. Self-expanding stents are also known which can expand from a first diameter to a larger second diameter without the use of a means for applying an interior radial force, such as a balloon, to them. One such type of self-expanding stent is a stent made of a shape memory metal which expands to its second larger diameter upon exposure to body temperature. Such stents are also known.

SUMMARY OF THE INVENTION

The present invention proposes a novel type of stent which combines a self-expanding part or portion with a part or portion which requires an interior radial force for expansion. More specifically, a stent for transluminal implantation according to the present invention will comprise cylindrical parts preferably in juxtaposition, with at least one part being self-expanding whereas another part requires an interior radial force for its expansion, such as a balloon catheter or the like. Basically, the stent will consist of at least two of the aforementioned parts but may consist of more than two parts. Such an arrangement enables improved placement of the stent by providing immediate expansion in part upon release of the stent from its delivery catheter.

DETAILED DESCRIPTION OF THE PREFERRED EMBODIMENTS

Figure 1:
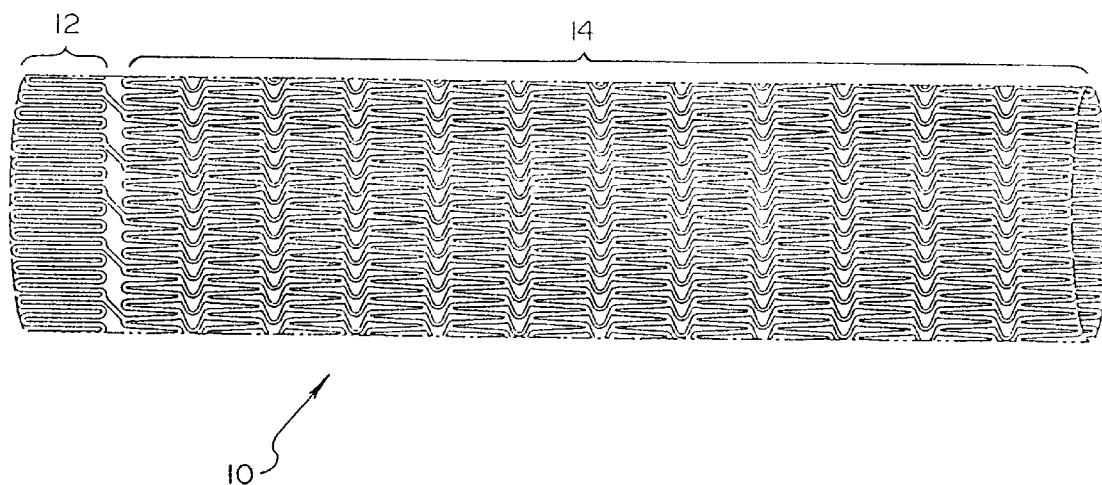
FIG. 1 is a showing of one embodiment of a stent according to this invention.

FIG. 1 shows a stent which combines self-expanding characteristics and balloon expandable characteristics, i.e., requires expansion by use of a radial interior force. Preferably, the stent will have the self-expanding part 12 joined at one end in juxtaposition to the proximal end of a balloon expandable stent 14. The parts of the stent may be formed in accordance with any of the known stents extant in the prior art. Preferably however, the self-expanding part 12 will be of a shape memory metal such as nitinol so as to enable self-expansion at body temperature upon release of the stent from its delivery catheter (not shown). The immediate expansion of part 12 aids in placement of the stent during release, following which a balloon or the like may be used to expand part 14.

Figure 2:
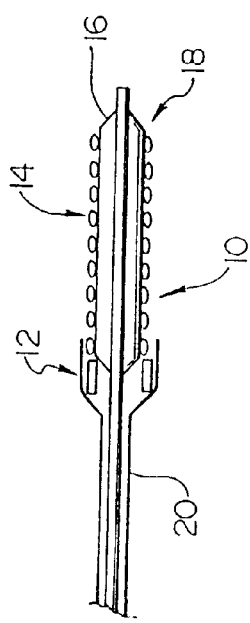
FIG. 2 is a schematic showing of a stent similar to that of FIG. 1 on a delivery catheter.
Figure 3:
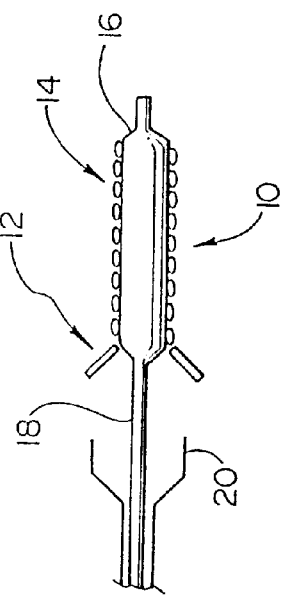
FIG. 3 is a schematic showing of the delivery system of FIG. 2 with the stent released for implantation.

Part 12 may be of a larger diameter, or it may be flared to provide the earliest possible contact with the body portion into which it is inserted, such as a vessel. This is best seen for example in FIGS. 2 and 3 which show a stent 10 similar to that of FIG. 1 on a delivery catheter. FIG. 2 shows the stent having the two parts 12 and 14, respectively. Part 12 is the self-expanding part while part 14 requires a separate force for expansion such as a balloon 16 of a delivery catheter generally indicated at 18 inside the stent. In FIG. 2, the stent is shown prior to release or deployment, the self-expanding part is enclosed by a retractable sheath 20. In FIG. 3, the sheath has been retracted, allowing self-expanding part 12 to flare-outwardly. Subsequently, balloon 16 may be used in the known manner to expand part 14.

Since most stent delivery catheters include a retractable sheath which exposes the stent for implantation and removal from the catheter, if the self-expanding part 12 is placed on the proximal end of the stent as shown, it will most likely be able to lock the stent in place until the remainder of the stent is expanded as by balloon expansion. This placement is preferable although placement in other parts of the stent proper may also be used.

Figure 4:
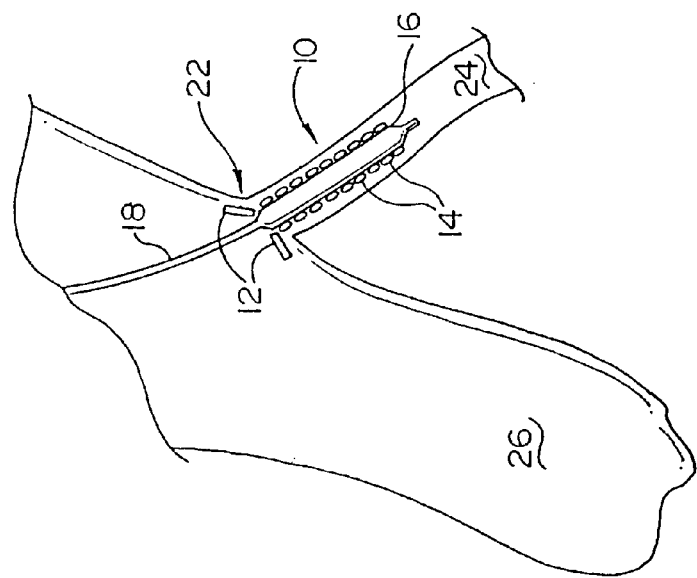
FIGS. 4 and 5 are schematic showings of a stent of the invention used in a vessel branching situation.
Figure 5:
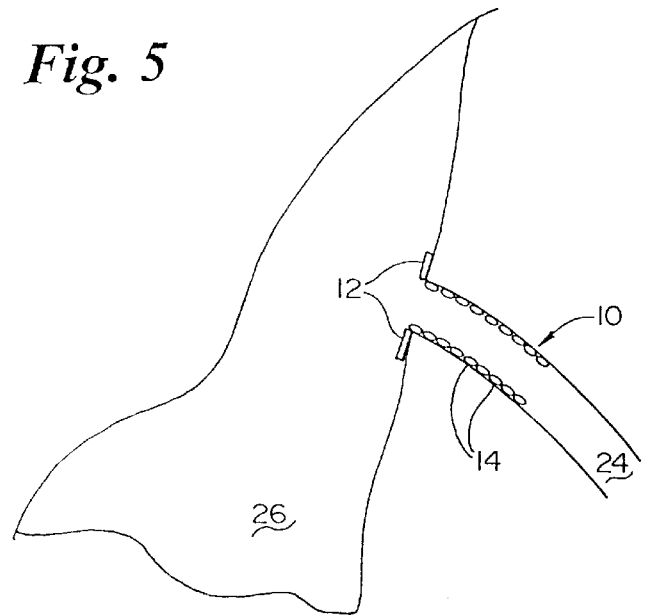

When the self-expanding portion is placed at the proximal end of the stent, such a stent is particularly useful in vessel stenting in which the vessel is of the bifurcating or branching type. Such a stent is shown schematically in FIGS. 4 and 5 at 10. FIG. 4 shows the stent having a proximal end part 12 which is self-expanding while the remainder of the stent body 14 is balloon expandable by balloon 16 on catheter 18. In FIG. 4, the retractable sheath has been removed allowing the self-expanding part to expand at the ostium 22 in a vessel 24 branching off of a main vessel such as aorta 26, helping to more accurately place the stent. FIG. 5 shows the stent after expansion of part 14 by the balloon catheter and catheter retraction. A stent according to the present invention allows positive placement of the stent near the ostium of the bifurcation.

Figure 6:
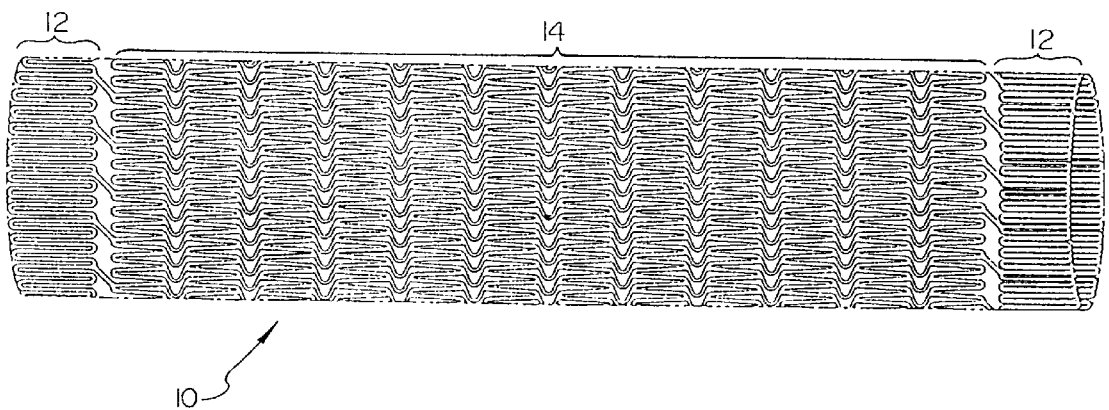
FIG. 6 is a showing of another embodiment of a stent according to the invention.

Stents according to the invention may also be comprised of more than one self-expanding and one balloon expandable part. Any combination of these parts is deemed to be within the scope of this invention. For example, referring to FIG. 6, a stent 10 is shown having a self-expanding part 12 at each end of a balloon expandable part 14.

Figure 7:
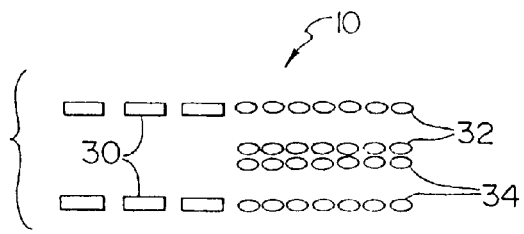
FIGS. 7–10 are schematic showings of bifurcated stents making use of the invention.

Referring now to FIGS. 7–10, bifurcated stents making use of the invention are described. Generally, bifurcated stents consist of three segments or components, a main trunk and two branches. In making use of this invention, any of the three components may be made to be balloon expandable or self-expandable, as desired. For example, FIG. 7 shows an unexpanded bifurcated stent 10 of one configuration in schematic form having a trunk 30, a first branch 32 and a second branch 34. As shown, trunk 30 is self-expanding, such as part 12 in the earlier Figures, and branches 32 and 34 are balloon expandable, such as part 14 in the earlier Figures.

Figure 8:
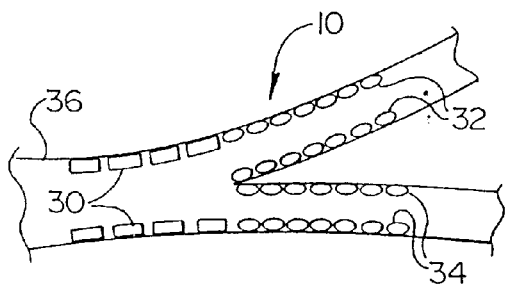

FIG. 8 shows the stent of FIG. 7 in an implanted position in a branching vessel 36.

Figure 9:
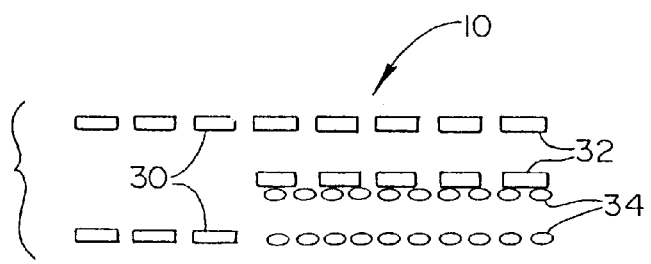

FIG. 9 shows another example of an unexpanded bifurcated stent 10 of another configuration in schematic form consisting of trunk 30 and branches 32 and 34. In this case, trunk 30 and branch 23 are both self-expanding and branch 34 is balloon expandable.

Figure 10:
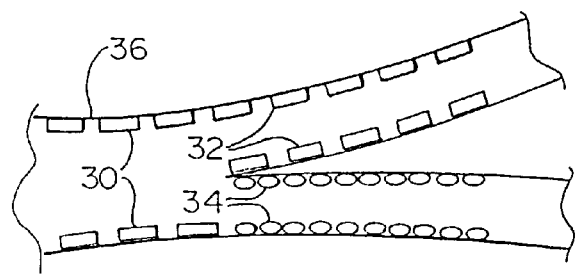

FIG. 10 shows the stent of FIG. 9 expanded in an implanted position in a branching vessel 36.

Trunk 30 in another embodiment may be balloon expandable while the branches 32 and 34 may be self-expandable.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent comprising at least a first portion which is self-expandable; a second portion which is balloon expandable and not self-expandable, the second portion connected to the first portion;

a first serpentine band which defines a first path about a lint circumference of the stent, the first path characterized by a first path length; and a second serpentine band which defines a second path about a second circumference of the stent, the second path characterized by a second path length, the first path length exceeding the second path length.

2. The stent of claim 1 wherein the first and second serpentine bands are connected by a plurality of connectors.

3. The stent of claim 2 wherein each connector has a first end and a second end, the first and second end longitudinally and circumferentially displaced from one another.

4. The stent of claim 3 wherein the connectors are linear.

5. The stent of claim 4 wherein the first serpentine band is self-expandable and the second serpentine band is balloon expandable.

6. The stent of claim 1 wherein the first serpentine band is characterized by a first amplitude and the second serpentine band is characterized by a second amplitude, the first amplitude different from the second amplitude.

7. The stent of claim 1 wherein the first portion is at a proximal or distal end of the stent.

8. The stent of claim 7 further comprising a second self-expandable portion.

9. The stent of claim 1 comprising a trunk portion, a first leg portion and a second leg portion.

10. The stent of claim 9 wherein the trunk portion is self-expandable.

11. The stent of claim 9 wherein one of the legs is self-expandable.

12. The stent of claim 9 wherein one of the legs is balloon expandable.

13. The stent of claim 1 wherein the self-expandable portion has a larger overall diameter than the rest of the stent.

14. The stent of claim 1 wherein the self-expanding portion is flared.

15. A stent having at least a first portion which is self-expandable and a second portion which is balloon expandable and not self-expandable, the second portion connected to the first portion, the stent comprising:

a first serpentine band, a second serpentine band, and a third serpentine band, the first serpentine band connected to the second serpentine band via a plurality of first connectors extending therebetween, the first connectors characterized by a first shape, the second serpentine band connected to the third serpentine band via a plurality of second connectors extending therebetween, the second connectors characterized by a second shape, wherein the first shape differs from the second shape.

16. The stent of claim 15 wherein the self-expandable portion comprises the first serpentine band and the balloon expandable portion comprises the second and third undulating bands.

17. The stent of claim 15 wherein the first connectors are linear and the second connectors include a curved portion.

18. The stent of claim 15 comprising a trunk portion, a first leg portion and a second leg portion.

19. The stent of claim 18 wherein the trunk portion is self-expandable and at least one leg portion is balloon expandable and not self-expandable.

20. A stent comprising at least a first portion which is self-expandable and a second portion which is balloon expandable and not self-expandable, the second portion connected to the portion, the first portion comprising a first serpentine shaped band and the second portion comprising a second serpentine shaped band, the second serpentine shaped band shaped differently than the first serpentine shaped band.

21. The stem of claim 20 wherein the first serpentine shaped band comprising a plurality of struts which are parallel to the longitudinal axis of the stent and the second serpentine shaped band comprises a plurality of struts which are non-parallel to the longitudinal axis of the stent.

* * * * *

UNITED STATES PATENT AND TRADEMARK OFFICE
CERTIFICATE OF CORRECTION

PATENT NO. : 6,409,755 B1
DATED : June 25, 2002
INVENTOR(S) : Anthony C. Vrba

It is certified that error appears in the above-identified patent and that said Letters Patent is hereby corrected as shown below:

<u>Column 3,</u>
Line 36, delete "lint" and insert -- first. --

<u>Column 4,</u>
Line 46, delete "the portion" and insert -- the first portion. --.
Line 51, delete "stem" and insert -- stent. --

Signed and Sealed this

Twenty-sixth Day of November, 2002

Attest:

Attesting Officer

JAMES E. ROGAN
*Director of the United States Patent and Trademark Office*